(12) United States Patent
Ise et al.

(10) Patent No.: US 6,599,752 B1
(45) Date of Patent: Jul. 29, 2003

(54) PROCESS FOR SEPARATING AND ANALYZING HYDROPHOBIC PROTEINS USING THIN LAYER CHROMATOGRAPHY

(75) Inventors: Wolfgang Ise, Constance (DE); Rüdiger Nave, Constance (DE); Wolfram Steinhilber, Stockach (DE)

(73) Assignee: Altana Pharma AG, Constance (DE)

( * ) Notice: Subject to any disclaimer, the term of this patent is extended or adjusted under 35 U.S.C. 154(b) by 25 days.

(21) Appl. No.: 09/190,455

(22) Filed: Nov. 13, 1998

Related U.S. Application Data

(63) Continuation-in-part of application No. PCT/EP97/02463, filed on May 14, 1997.

(30) Foreign Application Priority Data

May 15, 1996 (DE) ......................................... 196 19 576
Jun. 4, 1996 (EP) ............................................. 96108905

(51) Int. Cl.[7] .............................................. G01N 30/90
(52) U.S. Cl. ......................... 436/86; 435/7.1; 436/71; 436/162; 530/412
(58) Field of Search ................................ 436/161, 162, 436/71, 86; 530/412; 210/198.2, 198.3, 656, 658; 435/7.1

(56) References Cited

U.S. PATENT DOCUMENTS

| | | | | |
|---|---|---|---|---|
| 4,338,301 A | * | 7/1982 | Tetsuro | 424/95 |
| 4,384,994 A | * | 5/1983 | Veber et al. | |
| 4,849,509 A | * | 7/1989 | Thurin | 530/387 |
| 5,013,720 A | * | 5/1991 | Whitsett | |
| 5,258,496 A | * | 11/1993 | Benson | 530/350 |
| 5,422,262 A | * | 6/1995 | Andersson | 435/240.1 |
| 5,500,215 A | * | 3/1996 | Hakomori | |
| 5,648,457 A | * | 7/1997 | Takei | 530/324 |
| 5,726,018 A | * | 3/1998 | Pasternack | 435/6 |
| 6,121,004 A | * | 9/2000 | Pestronk | |

FOREIGN PATENT DOCUMENTS

WO 97/43313 * 11/1997

OTHER PUBLICATIONS

Chemical Abstract No. 1993:250974, Lou et al, Clin. Chem. (Washington, DC) (1993), 39(4), 619–24.*

* cited by examiner

*Primary Examiner*—Jan Ludlow
(74) *Attorney, Agent, or Firm*—Jacobson Holman PLLC

(57) ABSTRACT

This-layer chromatography is used to separate, identify and quantity hydrophobic protein, hydrophobic protein fragment, hydrophobic modified protein and hydrophobic peptide. A method is thus provided for determination of proteins and peptides which, due to their low solubility in an aqueous solvent system, cannot be determined by conventional methods, such as ELISA, which are based on aqueous solvent systems.

9 Claims, No Drawings

PROCESS FOR SEPARATING AND ANALYZING HYDROPHOBIC PROTEINS USING THIN LAYER CHROMATOGRAPHY

RELATED APPLICATION

This application is a continuation-in-part of International Application No. PCT/EP97/02463, filed May 14, 1997.

TECHNICAL FIELD

The invention relates to a process for the detection, identification and quantification of hydrophobic proteins, protein fragments and modifications, and of hydrophobic peptides.

PRIOR ART

The quantification of hydrophobic proteins is not possible or is only inadequately possible using conventionally customary techniques. The customary methods for separation of hydrophilic proteins, such as Western blotting, are often only applicable to hydrophobic proteins to a limited extent, because on the one hand separation on SDS gel is inadequate and on the other hand transfer of the proteins to customary membranes can be described as at most semiquantitative. A separation of slightly modified proteins (e.g., methyl esters) cannot be effected by means of gel electrophoresis. The use of immunological methods, such as ELISA, is very problematical; as a rule this can only be carried out in aqueous systems. Organic solvents may react with material of microtiter plates and render them unusable. The analytes to be quantified are usually present only in traces. Often, straight hydrophobic proteins are additionally associated with other lipophilic substances (e.g., lipids), which makes quantification according to conventional methods impossible. In ELISA, the components are not separated from one another.

SUMMARY OF THE INVENTION

The aim of the invention is to provide a process which allows even strongly hydrophobic proteins, protein fragments and modifications and also strongly hydrophobic peptides to be separated, identified and quantified.

A further aim is to make available a process which makes possible the determination and quantification of, for example, proteins which are slightly modified by acetylation or oxidation.

It is a further aim to provide a process which is suitable, in particular, for the determination of hydrophobic host-cell protein impurities (HCP) in the biotechnological production of hydrophobic proteins, such as the extremely hydrophobic lung surfactant protein SP-C.

These aims are achieved by thin-layer chromatographic separation of a protein mixture dissolved in an organic medium and immunological quantification of the separated proteins.

The object of the invention is therefore a process for the separation, identification and quantification of strongly hydrophobic proteins, protein fragments and modifications and also of strongly hydrophobic peptides, which comprises dissolving the samples to be investigated in an organic medium, subjecting them to thin-layer chromatography and rendering the hydrophobic proteins visible immunologically.

DETAILS

It has surprisingly been found that, for the thin-layer chromatographic separation step, procedures and materials known per se which are adapted to the hydrophobic properties of the proteins to be separated lead to the desired result. Appropriate chromatography plates include all plates having a coating suitable for separation of hydrophobic mixtures in organic media. Examples of such plates are those which have chemically-modified silicon layers, such as HPTLC plates named Diol, CN, NH2, RP-2, RP-8 and RP-18. Of these, those which prove particularly suitable are the HPTLC plates marketed by Merck Darmstadt under the trade name Diol, which have a modified silica matrix. For hydrophobic proteins, suitable mobile phases for thin-layer chromatography are organic solvents and solvent mixtures, e.g., of chloroform and methanol. Mixtures of nonpolar and polar solvents are particularly expedient, possible nonpolar solvents, in particular, being chloroform, methylene chloride and toluene, and polar solvents being shortchain alcohols, particularly methanol, ethanol and isopropanol.

Hydrophobic proteins, protein fragments and modifications and hydrophobic peptides refers to proteins, protein fragments and protein modifications and peptides which, without the aid of a detergent, are poorly soluble in aqueous solvent systems, such as membrane proteins. Surfactant protein C is such a hydrophobic protein. By "strongly hydrophobic" is meant proteins, protein fragments and protein modifications or peptides which are essentially insoluble in an aqueous solvent system.

In the process for preparing surfactant protein C, impurities which consist of host cell proteins are encountered. These have a hydrophobicity similar to that of r-SP-C. Protein fragment refers to a protein which forms part of a complete sequence of a naturally occurring or artificial (synthetic) protein. Protein modification refers to a protein which differs by addition, substitution or deletion of one or more amino acids or chemical modifications, like alkylation, acylation, esterification and oxidation (for example, oxidation of thio radicals) of amino acids, as compared to the naturally occurring or artificial protein. Example: r-SP-C disclosed in WO 95/32992 (copending U.S. application Ser. No. 08/750,194 filed Nov. 27, 1996 now U.S. Pat. No. 5,874,406) is a modification of natural (human) SP-C.

The application of the samples to plates and the separation procedure are carried out in a customary manner, for example by means of commercially available automatic equipment.

Primary antibody/immunological method: The detection step in the process can be carried out in different ways. When an immunological detection method is used, it is carried out with the help of an antibody which (preferably specifically) binds the hydrophobic protein. (HP) to be detected. To this end the thin layer chromatography (TLC) plates are incubated with a (primary) antibody having specificity to the hydrophobic protein. This antibody can carry a label, and this label then provides the basis for detection. If this antibody does not carry a label, a second antibody (carrying a label), having specificity to the first antibody, can be used for detection. Such methods for immunological detection of proteins using antibodies are well known in the art and are, for example, applied in ELISA tests and Western. blotting analyses. The kind of (primary) antibody depends on the kind of hydrophobic protein to be detected. The second antibody will be an anti-"primary antibody"-antibody.

Besides immunological detection, the detection of the hydrophobic protein on a plate is also achieved by way of conventional staining with a suitable reagent. Reagents used for staining of proteins are well known in the art and include, e.g., Coomassie, Ponceau S and silver.

For preparation for immunological detection, the plates are dried after thin-layer chromatographic separation. For the saturation of nonspecific binding sites, the plates are incubated with a suitable blocking solution, e.g. gelatin or protein. The plates are then incubated with the primary antibody. If this does not carry a label, detection can be carried out with the aid of a labeled second antibody. For detection, all commercially available detection processes can be used. After removal of excess first antibody by washing, incubation is carried out with a labeled second antibody. After washing, the labeled antibodies are detected. They are visualized in a customary manner, e.g., by addition of luminol and hydrogen peroxide, for example with the aid of the ECL (enhanced Chemiluminescence) detection process of Amersham Buchler, which is very sensitive. In a purity analysis, with a view to slight chemical modifications, the substances are also detected on TLC plates directly after separation using customary protein staining reagents.

In the following text, the invention is described by example with the aid of a process for the determination of the host-cell protein impurities in a biotechnological process for the preparation of r-SP-C by means of $E.\ coli.$ r-SP-C refers to recombinant surfactant protein C or modified derivatives of r-SP-C.

The process is advantageously applied in the detection of hydrophobic impurities (hydrophobic host cell proteins) which are encountered in the production of r-SP-C with the host cells, such as $E.\ coli.$ Such process for production of r-SP-C is, for example, disclosed in WO 95/32992 (copending application Ser. No. 08/750,194, pages 10 to 12), which shows how to obtain the starting material for the following example. The example (step 1) describes the preparation of antigens (HCP antigens) which are used for the generation of the antibodies (primary antibody) against HCP impurities (step 2). Such antibodies are required in the immunological detection step of the subject process when it is desired to detect HCP impurities.

EXAMPLE

1. Obtainment of HCP for Immunization Purposes

In agreement with procedures known from the literature and with relevant official regulations, an antigen fraction from the final phase of the downstream process was sought. Therefore, for immunization, HCPs are withdrawn from a fermentation phase in which the r-SP-C is pure to 80 to 90%. For removal of the HCP antigen fraction, 60 g of inclusion bodies isolated by filtration and/or centrifugation from a 10 l blank fermentation are used after lyophilization for about 96 hours.

2. Preparation of Antisera 1 mg of HCP, dissolved in 95% strength isopropanol of pH 2, is dried in a vacuum concentrator (Speedvac®), resuspended in 0.5 ml of phosphate-buffered saline, mixed with 0.5 ml of adjuvant (ABM-S for base immunization and ABM-N for booster injections) and in each case is injected subcutaneously in an amount of 1 mg/rabbit. The immunization scheme is carried out according to standard protocols: after the primary immunization, booster injections are carried out every 4 weeks up to six times. Taking of blood is, in each case, carried out 10 days after the last injection in order to monitor the development of the titer. As soon as the titer is satisfactory, 50 ml of blood are taken, and serum is prepared according to standard procedures.

3. Determination of the Titer

For determination of the titer, the individual sera at various dilutions are analyzed by means of a new method described as immuno-thin-layer chromatography (immuno-TLC). Dilutions of 1:5000, 1:1000, 1:20,000 and 1:50,000 are used in order to analyze 4, 15, 62.5 and 250 ng of HCP. At a dilution of 1:10,000 all rabbit antibodies investigated recognize HCP components in proportion to the amount of total protein. Antisera having a similar titer are pooled and reanalyzed. The serum is characterized according to stardard procedures and stored in aliquots at −20° C. (The term "immuno-TLC" refers to the subject process when an immunological method is used in the detection step.)

4. Sample Preparation and Thin-layer Chromatography (TLC)

The samples to be analyzed are dried in a vacuum concentrator and dissolved in 20 to 200 µl of $CHCl_3$/MeOH. For thin-layer chromatography, HPTLC plates having a modified silica matrix, such as are marketed by Merck Darmstadt, under the trade name Diol, are used. The application of the samples to the HPTLC plates is carried out automatically using a Lingomat IV (Camag, Berlin). After sample application, the plates are air-dried and subjected to chromatography using a $CHCl_3$/MeOH mixture [$CHCl_3$/MeOH/25% strength $NH_4OH/H_2O$=32.5/15/1/2 (ratio by volume)] as the liquid phase. After chromatography, the plates are dried.

5. 2Immunostaning of HCP with Anti-HCP Antibodies

For the saturation of nonspecific binding sites, the dried HPTLC plates are incubated for 4 hours with 3% strength fish gelatin in PBS which contains 150 mM NaCl, 12 mM $Na_2HPO_4$ and 3 mM $NaH_2PO_4$ (pH 7.4). The plates are then incubated overnight and lightly shaken in the presence of the primary antibody, usually at a dilution of 1:10,000. Unbound antibodies are removed by washing several times with Tris Buffer Saline/Tween (TBS/T) from 4 mM tris HCl, 100 mM NaCl, 0.05% Tween 20 (pH 7.4). For hybridation with the primary antibody, the plates are incubated for 2 hours with horseradish peroxidase-conjugated secondary antibody at a dilution of 1:80,000 in the TBS/T. Unbound antibodies are removed, as described above, by washing the plates several times with TBS/T. Immunoreactive complexes are visualized using an ECL detection system from Amersham Buchler. The plates are incubated for 20 to 50 seconds with an X-ray film (Hyperfilm Amersham).

6. Staining and Immunological Detection of SP-C

In order to detect modifications of SP-C (e.g., methyl ester at the C-terminus and methionine sulfoxide), the protein forms separated by means of TLC are detected by means of staining with Ponceau S. A more sensitive alternative is the use of SP-C antibodies and of the method indicated above in analogy to HCP determination.

7. Video-imaging of the X-ray Films and Computer Analysis

For the quantification of the immune complexes, the X-ray films are digitalized using a video-imager (Cybertech, Berlin, Germany). The signal intensities on the X-ray films are analyzed by computer analysis using Wincam software (Cybertech).

8. Quantification of HCP

For the determination of HCP in r-SP-C samples, aliquots are analyzed pure or after addition of 2.5, 5.0 or 10.0 ng of HCP. The amounts of HCP in the individual samples are determined by linear regression calculations. Percentages are determined by means of the formula %=(ng of HCP× 100)/ng of r-SP-C.

In order to quantify small amounts of HCP in r-SP-C, it is necessary to separate the majority of the target protein from the small amount of HCP. This is effected by thin-layer chromatography. The detection limit for HCP is analyzed by mixing 5 µg of highly pure r-SP-C with ng amounts of HCP. Under these conditions, 0.125 ng of HCP is the smallest amount which it is possible to differentiate from the endogenous HCP content of r-SP-C. The amount of the sample which can be analyzed by immunoTLC depends on the HCP content. For r-SP-C samples which contain less than 0.1% of HCP, 1 to 5 µg of r-SP-C are analyzed. Since amounts of r-SP-C up to 20 µg can be separated by thin-layer chromatography and the quantification limit is 1 ng on luminography (when using 5 µg of added r-SP-C), it is theoretically possible to detect HCP down to 0.005%. The detection of 0.002% HCP appears to be a reliable quantification limit under standard conditions.

The invention and its advantages are readily understood from the forgoing description. Various changes may be made in the disclosed process without departing from the spirit and scope of the invention or sacrificing its material advantages. The described process is merely illustrative of a preferred embodiment.

What is claimed is:

1. A process which comprises separation, determination and quantification of a hydrophobic host-cell protein impurity in a biotechnological product of hydrophobic proteins, and wherein a sample to be investigated is dissolved in an organic medium and subjected to thin layer chromatography (TLC); the hydrophobic host-cell protein impurity is immunologically detected directly on a TLC plate, and said hydrophobic host-cell protein is quantified.

2. A process as claimed in claim 1 wherein the organic medium is a mixture of chloroform and methanol.

3. A process as claimed in claim 1 wherein the quantification is effected by an immunological method.

4. A process as claimed in claim 3 wherein the immunological method comprises binding the hydrophobic host-cell protein impurity to optionally labeled antibody.

5. A process as claimed in claim 4 which comprises visualizing and quantifying immunoreactive complexes.

6. A process as claimed in claim 5 wherein the visualizing and quantifying are effected with the aid of enhanced chemiluminescence.

7. A process as claimed in claim 1 which comprises effecting the thin layer chromatography on coated plates having a modified silicon matrix.

8. A process as claimed in claim 1 wherein the hydrophobic host-cell protein impurity is highly hydrophobic.

9. A process as claimed in claim 8 wherein the organic medium is a mixture of solvents in which the hydrophobic host-cell protein impurity is soluble.

* * * * *